(12) United States Patent
Harmoko et al.

(10) Patent No.: US 11,052,187 B2
(45) Date of Patent: Jul. 6, 2021

(54) PACKAGING FOR A REEL OF MEDICAL INJECTION DEVICES

(71) Applicant: Becton Dickinson Holdings Pte. Ltd., Singapore (SG)

(72) Inventors: Hendri Harmoko, Singapore (SG); Benjamin Yang Teck Tan, Singapore (SG); Dexter Chew Xuan Han, Singapore (SG); Stacey Ng Zhi Min, Singapore (SG)

(73) Assignee: Becton Dickinson Holdings Pte. Ltd., Singapore (SG)

( * ) Notice: Subject to any disclaimer, the term of this patent is extended or adjusted under 35 U.S.C. 154(b) by 117 days.

(21) Appl. No.: 16/486,567

(22) PCT Filed: Feb. 14, 2018

(86) PCT No.: PCT/SG2018/000002
§ 371 (c)(1),
(2) Date: Aug. 16, 2019

(87) PCT Pub. No.: WO2018/151671
PCT Pub. Date: Aug. 23, 2018

(65) Prior Publication Data
US 2019/0374702 A1    Dec. 12, 2019

(30) Foreign Application Priority Data
Feb. 20, 2017    (EP) .................... 17156988

(51) Int. Cl.
*A61M 5/00* (2006.01)
*B65B 31/00* (2006.01)
(Continued)

(52) U.S. Cl.
CPC ............. *A61M 5/002* (2013.01); *B65B 31/00* (2013.01); *B65D 61/00* (2013.01); *B65D 77/04* (2013.01);
(Continued)

(58) Field of Classification Search
CPC ......... A61M 5/00; A61M 5/002; B65B 31/00; B65D 61/00; B65D 77/04; B65D 81/20; B65D 81/2007; B65D 85/671
(Continued)

(56) References Cited

U.S. PATENT DOCUMENTS 2,916,152 A    12/1959    Dull
4,829,909 A    5/1989    Mandel
(Continued)

FOREIGN PATENT DOCUMENTS

| CN | 208470370 U | 2/2019 |
| WO | 2010067033 A1 | 6/2010 |
| WO | 2018151671 A1 | 8/2018 |

*Primary Examiner* — Bryon P Gehman
(74) *Attorney, Agent, or Firm* — The Webb Law Firm

(57) ABSTRACT

A packaging for a reel of medical injection devices includes a base tray configured for supporting the reel and at least a first flat rib and a second flat rib. Each rib includes a respective slot arranged such that the ribs can be interlocked with one another by mutual engagement of the slots. The base tray includes at least two pairs of peripheral openings. Each opening is configured to receive an end of the ribs, so that the base tray and interlocked flat ribs engaging the base tray form a frame configured for enclosing the reel.

10 Claims, 3 Drawing Sheets

(51) Int. Cl.
*B65D 61/00* (2006.01)
*B65D 77/04* (2006.01)
*B65D 81/20* (2006.01)
*B65D 85/671* (2006.01)

(52) U.S. Cl.
CPC ....... *B65D 81/2007* (2013.01); *B65D 85/671* (2013.01)

(58) Field of Classification Search
USPC .................................. 206/370, 438, 389–416
See application file for complete search history.

(56) References Cited

U.S. PATENT DOCUMENTS

| | | | |
|---|---|---|---|
| 8,211,038 B2 * | 7/2012 | Wang | A61B 5/1486 600/584 |
| 10,647,489 B2 * | 5/2020 | Shimizu | B65D 73/02 |

* cited by examiner

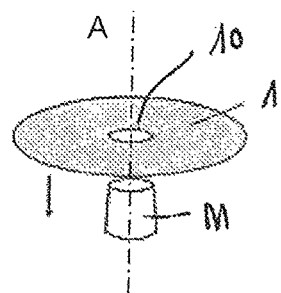
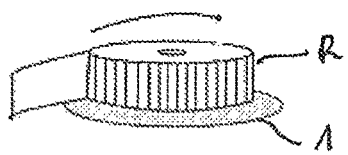
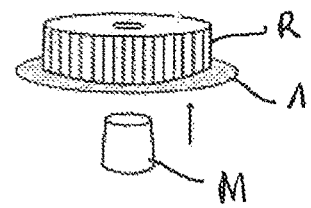
FIGURE 5A　　　　FIGURE 5B　　　　FIGURE 5C
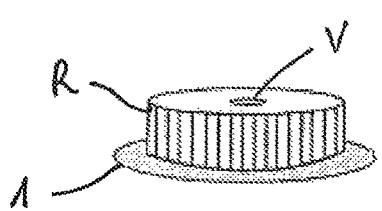
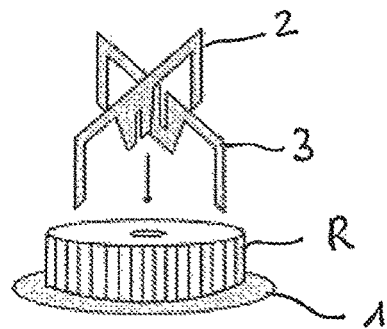
FIGURE 5D　　　　FIGURE 5E
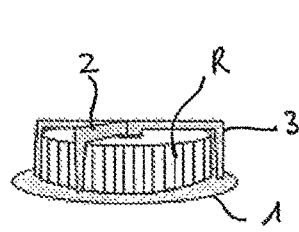
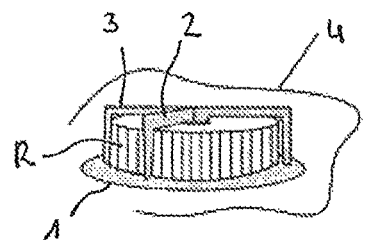
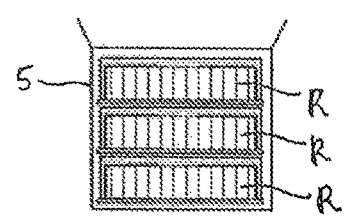
FIGURE 5F　　　　FIGURE 5G　　　　FIGURE 5H

PACKAGING FOR A REEL OF MEDICAL INJECTION DEVICES

CROSS-REFERENCE TO RELATED APPLICATIONS

This application is the United States national phase of International Application No. PCT/SG2018/000002 filed Feb. 14, 2018, and claims priority to European Patent Application No. 17156988.2 filed Feb. 20, 2017, the disclosures of which are hereby incorporated by reference in their entireties.

FIELD OF THE INVENTION

The invention relates to a packaging for a reel of medical injection devices, and a process for manufacturing such a packaging.

BACKGROUND OF THE INVENTION

BD Uniject™ disposable medical injection devices are collectively provided in the form of a reel, each device being intended to be separated from the reel in order to be used.

The current packaging is illustrated in FIG. 1. The arrows show successive steps of the manufacturing process of said packaging.

The packaging comprises a base tray 100 that supports the reel R. The base tray 100 comprises a central protrusion 101 around which the reel R is wrapped.

The packaging further comprises a cover 200 in the form of a planar sheet arranged on the side of the reel R opposite the base tray 100.

The base tray 100, reel R and cover 200 are then introduced in a polyethylene bag 300 that is vacuum sealed in order to maintain sterility of the medical injection devices D.

Said packagings can then be stacked on each other into cardboard boxes. Bubble wrap is used to protect the medical injection devices of each packaging from shocks that could generate crashing and/or unintentional activation of the devices.

However, there remains a need for reducing the material used, the weight and cost of such a packaging.

SUMMARY OF THE INVENTION

A goal of the invention is to provide a packaging that allows savings in terms of material used, weight and cost, without substantially affecting the manufacturing process of the reels. This improved packaging should also allow protecting the medical injection devices from crashing and/or from unintentional activation.

Accordingly, the invention provides a packaging for a reel of medical injection devices, comprising a base tray for supporting said reel, characterized in that it further comprises at least two flat ribs each comprising a respective slot arranged such that the ribs can be interlocked with one another by mutual engagement of said slots, and in that the base tray comprises at least two pairs of peripheral openings, each opening being configured to receive an end of a rib, so that the base tray and interlocked flat ribs engaging the base tray form a frame configured for enclosing the reel.

By "flat" is meant that the main surfaces of the ribs extend in parallel planes, without any protrusion arising out from said planes.

According to an embodiment, the base tray is circular and both openings of each pair of peripheral openings are diametrically opposite.

Preferably, the two pairs of peripheral openings are arranged such that the interlocked flat ribs engaging the base tray are perpendicular to each other.

According to an embodiment, each flat rib comprises a central foot, the respective slot being arranged in said central foot, and the base tray comprises a central opening configured to receive the central feet of the interlocked flat ribs.

The central foot of each flat rib has a first side opposite the base tray, and a second side opposite the first side, and the slot of a first rib extends from the first side of the foot, and the slot of a second rib extends from the second side of the foot.

According to an embodiment, the base tray and the flat ribs are made from a corrugated polystyrene sheet.

Alternatively, the base tray and the flat ribs may be made from corrugated cardboard.

Another object of the invention is a process for manufacturing such a packaging, comprising:
providing the base tray;
arranging the reel of medical injection devices onto the base tray;
slotting each flat rib onto the base tray, thereby interlocking the ribs via their respective slots, so as to maintain the reel of medical injection devices between the base tray and the interlocked ribs.

According to an embodiment, said process further comprises forming at least one of the base tray and the flat ribs by die-cutting a corrugated polystyrene or cardboard sheet.

In addition, the process may further comprise enclosing the base tray, the reel of medical injection devices and the interlocked ribs in a vacuum sealed bag.

BRIEF DESCRIPTION OF THE DRAWINGS

Other features and advantages of the invention will be apparent from the detailed description that follows, based on the appended drawings wherein:

FIGS. 5A to 5H schematically illustrate process steps for packaging a reel of BD Uniject™ disposable medical injection devices.

DETAILED DESCRIPTION OF EMBODIMENTS OF THE INVENTION

Figure 2:
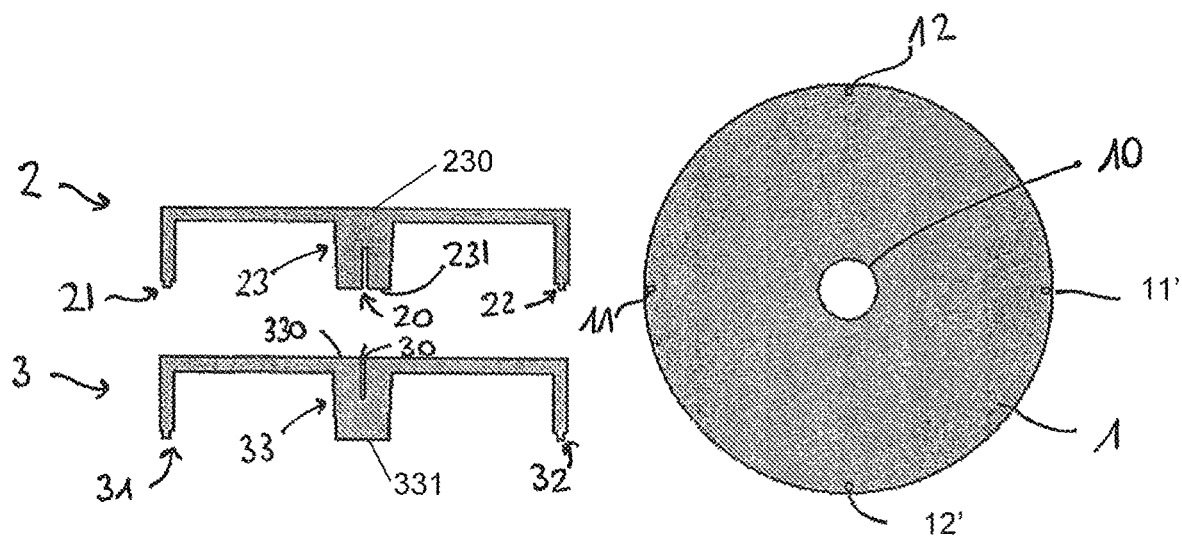
FIG. 2 schematically illustrates components of a packaging according to an embodiment of the invention.

FIG. 2 illustrates the main components of a packaging for a reel of medical injection devices according to an embodiment of the invention.

The packaging mainly comprises three components: a tray 1 and two interlocked flat ribs 2 and 3 engaging the tray 1 so as to maintain the reel R of medical injection devices between the tray 1 and the ribs 2 and 3.

The medical injection devices may be BD Uniject™ single-use medical injection devices or any other medical injection devices provided as a reel.

As will be seen in more detail below, the tray 1 and ribs 2, 3 are flat, which means that they can be manufactured with a very simple and cheap process, e.g. by die-cutting a sheet of a suitable material, such as corrugated polystyrene or corrugated cardboard. The thickness of said sheet is of about 6 mm. Of course, the tray 1 and ribs 2, 3 could be manufactured by another suitable process, such as molding, without departing from the scope of the present invention.

The tray 1 generally presents a disc shape, with a diameter larger than the diameter of the reel R of medical injection devices.

The tray 1 comprises two pairs of peripheral openings 11, 11', 12, 12' arranged such that the openings of each pair of peripheral openings 11, 11', and 12, 12' are diametrically opposite. Preferably, adjacent openings are arranged at 90° with respect to each other. The distance between the openings of each pair is greater than the diameter of the reel R of medical injection devices.

The ribs 2, 3 have substantially the same general shape, including a central foot 23, 33 from which extend two angled arms. Each arm extends on both sides of the central foot 23, and has a first portion that is substantially perpendicular to the central foot and a second portion substantially perpendicular to the first portion. Each end 21, 22, 31, 32 of the arms of ribs 2, 3 are configured so as to engage a respective opening 11, 11', 12, 12' of the tray 1.

To that end, the shape and size of the ends 21, 22, 31, 32 are selected to substantially match the shape and size of the openings 11, 11', 12, 12'. Preferably, the size of the openings 11, 11', 12, 12' is slightly greater than the size of the ends 21, 22, 31 32 so as to allow an easy insertion of the ribs 2, 3 onto the tray 1.

Figure 3:
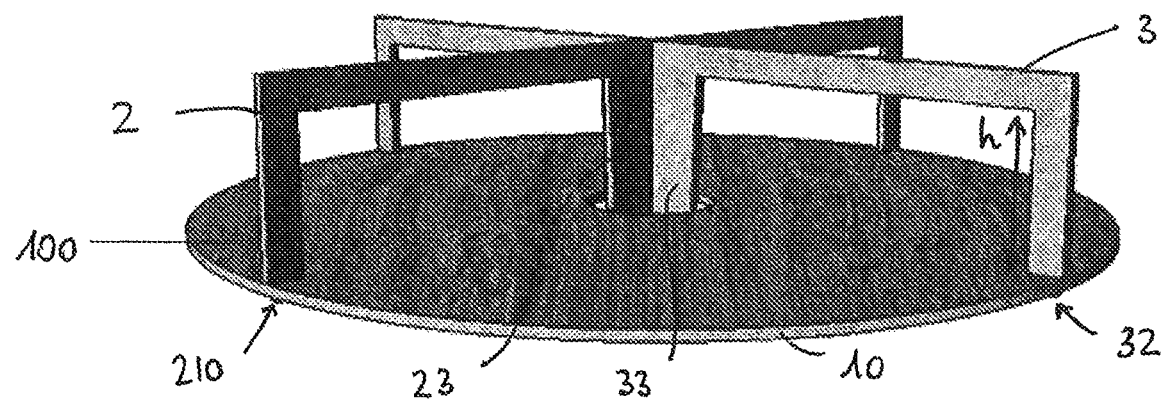
FIGS. 3 and 4 schematically illustrate a packaging according to an embodiment of the invention, without and with the injection devices.
Figure 4:
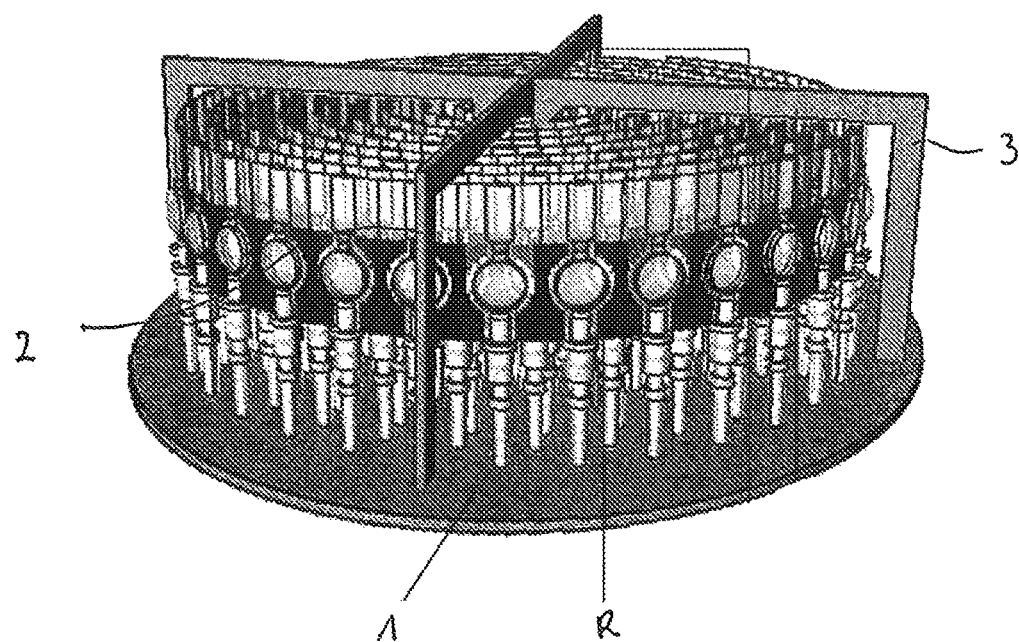

Advantageously, the ends 21, 22, 31, 32 are provided with an abutment in order to control the depth of their insertion with respect to the tray 1. This allows controlling the distance h between the ribs 2, 3 and the tray 1, which must be sufficient to contain the reel R without exerting any pressure onto the medical containers (see FIGS. 3 and 4).

The ribs 2, 3 comprise a respective slot 20, 30 provided in the central foot 23, 33 such that the ribs 2, 3 can be interlocked with one another by mutual engagement of said slots 20, 30.

To that end, the slot 20 of rib 2 extends from the base 231 of the central foot 23 that faces the tray, up to the middle of the central foot 23.

Accordingly, the slot 30 of rib 3 extends from the top 330 of the central foot 33, which is oriented opposite the tray, down to the middle of the central foot. The base of the foot 33 opposite to the top 330 is referred to as 331.

The width of the slots 20, 30 substantially correspond to the thickness of the ribs 2, 3.

Thus, when the rib 2 is put over the rib 3 such that the slots 20, 30 engage each other, the ribs 2, 3 form a substantially stable and stiff assembly, the ribs 2, 3 being retained by mutual friction. At the same time, the ends 21, 22, 31, 32 are engaged into the openings 11, 11', 12, 12' of the tray 1.

Preferably, the interlocked ribs 2, 3 are perpendicular to each other.

Advantageously, the sides 230, 330 of the ribs 2, 3 opposite the tray 1 are linear and the slots 20, 30 are configured such that in the interlocked configuration of the ribs, the sides 230, 330 are coplanar. As a result, the sides 230, 330 can form a support surface for a flat tray of another packaging stacked onto them.

According to a preferred embodiment, as visible on FIG. 2, the tray 1 further comprises a central opening 10, which is for example circular.

Figure 1:
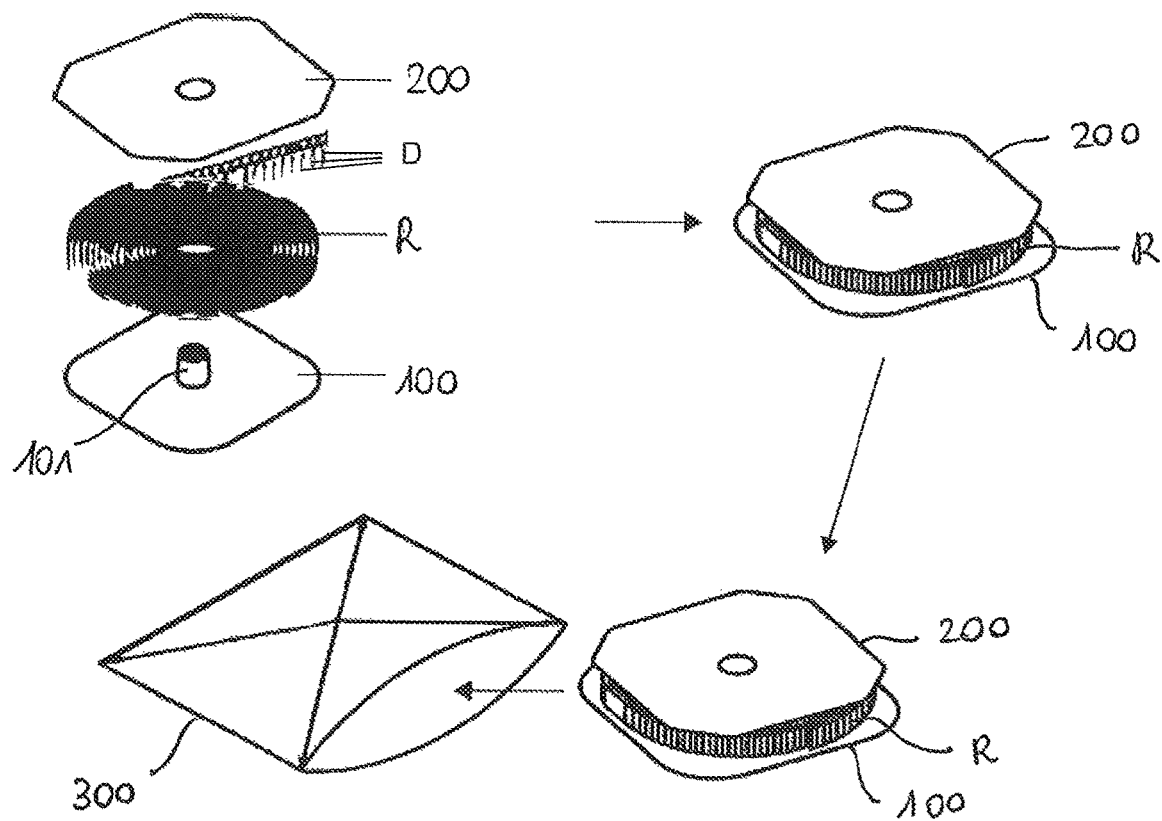
FIG. 1 is a schematic view of a packaging for BD Uniject™ disposable medical injection devices according to the prior art.

When the different components of the packaging are assembled, the opening 10 receives the central feet 23, 33 of the interlocked ribs 2, 3. The reel R of medical injection devices thus extends around the central feet 23, 33. This arrangement with the packaging of the invention allows further stabilizing the reel of medical injection devices in the packaging. Besides, the tray 1 is thus simpler and quicker to manufacture than the tray 100 known from the prior art, as visible on FIG. 1.

FIGS. 5A-5H show successive steps of the manufacturing process of the packaging of the invention.

With reference to FIG. 5A, the tray 1 is mounted on a winding machine (not shown), the central opening 10 engaging a mandrel M of the winding machine (the arrow shows the direction of insertion of the tray onto the longitudinal axis A.

With reference to FIG. 5B, the reel R of medical injection devices is wrapped (as shown by the arrow) around the mandrel M of the winding machine and lies onto the tray 1. The step of winding the reel is substantially the same as in the prior art, apart from the fact that since the tray 1 is flat, the central protrusion 101 of the prior art tray 100 is replaced by the mandrel M.

With reference to FIG. 5C, the tray 1 with the reel R are removed from the mandrel M (see direction indicated by the arrow).

As can be seen in FIG. 5D, there thus remains a central void V in the reel R, corresponding to the mandrel M of the winding machine.

With reference to FIG. 5E, ribs 3 and 2 are assembled with the tray 1 (see direction indicated by the arrow) supporting the reel R of the medical injection devices, the central feet 23, 33 being interlocked by the slots 20, 30 and engaging the central void V of the reel R and the central opening 10 of the tray 1. Meanwhile, the ends 21, 22, 31, 32 of the ribs 2, 3 engage the peripheral openings 11, 11', 12, 12' of the tray 1.

The assembly comprising the packaging of the invention together with the reel R of medical injection device is shown in FIG. 5F.

With reference to FIG. 5G, the assembly is enclosed into a bag 4 and is then vacuum sealed. Such a bag is known per se and comprises for example two polyethylene layers. The medical injection devices are thus protected from external contamination.

The manufacturing steps described above are generally performed in a clean room.

With reference to FIG. 5H, a plurality of such assemblies (each enclosed in a respective vacuum sealed bag) can be stacked onto each other in a cardboard box 5 for storage and/or shipping.

With the packaging of the invention the medical injection devices are protected from shocks and pressure by the three-dimensional skeletal structure formed by the two-dimensional tray and ribs of each packaging. Thus, crashing or unintentional activation of the medical injection devices can be avoided.

In particular, on the one hand, the tray of a packaging bears in a stable way onto the right-angled interlocked ribs of an underlying packaging. On the other hand, since the ribs also extend along the periphery of the reel, they provide a peripheral protection of the medical injection devices. Besides, the weight of the packaging is substantially reduced as compared to the prior art packaging.

As a result, the packaging according to the invention allows reducing use of bubble wrap in the cardboard boxes, while being very simple and cheap to manufacture and assemble.

The invention claimed is:

1. A packaging for a reel of medical injection devices, comprising a base tray configured for supporting the reel, the packaging further comprising at least a first flat rib and a second flat rib, each rib comprising a respective slot arranged such that the ribs can be interlocked with one another by mutual engagement of the slots, wherein the base tray comprises at least two pairs of peripheral openings, each opening being configured to receive an end of the ribs, so that the base tray and interlocked flat ribs engaging the base tray form a frame configured for enclosing the reel.

2. The packaging of claim 1, wherein the base tray is circular and both openings of each pair of peripheral openings are diametrically opposite.

3. The packaging of claim 2, wherein the two pairs of peripheral openings are arranged such that the interlocked flat ribs engaging the base tray are perpendicular to each other.

4. The packaging according to claim 1, wherein each flat rib comprises a central foot, the respective slot being arranged in the central foot, and the base tray comprises a central opening configured to receive the central feet of the interlocked flat ribs.

5. The packaging according to claim 4, wherein the central foot of each flat rib has a first side opposite the base tray, and a second side opposite the first side, and the slot of a first rib extends from the first side of the foot, and the slot of a second rib extends from the second side of the foot.

6. The packaging of claim 1, wherein the base tray and the flat ribs are made from a corrugated polystyrene sheet.

7. The packaging of claim 1, wherein the base tray and the flat ribs are made from corrugated cardboard.

8. A process for manufacturing the packaging of claim 1, comprising:
   providing the base tray;
   arranging the reel of medical injection devices onto the base tray;
   slotting each flat rib onto the base tray, thereby interlocking the ribs via their respective slots, so as to maintain the reel of medical injection devices between the base tray and the interlocked ribs.

9. The process of claim 8, further comprising forming at least one of the base tray and the flat ribs by die-cutting a corrugated polystyrene or cardboard sheet.

10. The process of claim 8, further comprising enclosing the base tray, the reel of medical injection devices and the interlocked ribs in a vacuum sealed bag.

* * * * *